(12) United States Patent
Marasco

(10) Patent No.: US 8,568,375 B2
(45) Date of Patent: Oct. 29, 2013

(54) WOUND TREATMENT AND CONTAINMENT ARRANGEMENT

(75) Inventor: Patrick V. Marasco, Boxford, MA (US)

(73) Assignee: Pulsecare Medical, N. Andover, MA (US)

( * ) Notice: Subject to any disclaimer, the term of this patent is extended or adjusted under 35 U.S.C. 154(b) by 448 days.

(21) Appl. No.: 12/806,290

(22) Filed: Aug. 9, 2010

(65) Prior Publication Data

US 2011/0071426 A1 Mar. 24, 2011

Related U.S. Application Data

(63) Continuation-in-part of application No. 11/232,456, filed on Sep. 21, 2005, now Pat. No. 7,771,402, which is a continuation-in-part of application No. 10/684,960, filed on Oct. 14, 2003, now abandoned, which is a continuation-in-part of application No. 09/621,636, filed on Jul. 21, 2000, now Pat. No. 6,635,035, which is a continuation-in-part of application No. 09/561,978, filed on May 2, 2000, now Pat. No. 6,562,013, which is a continuation-in-part of application No. 09/156,115, filed on Sep. 18, 1998, now Pat. No. 6,083,209, which is a continuation-in-part of application No. 08/682,888, filed on Jul. 11, 1996, now Pat. No. 5,848,998.

(51) Int. Cl.
*A61M 35/00* (2006.01)

(52) U.S. Cl.
USPC ........... 604/289; 128/202.12; 128/205.26

(58) Field of Classification Search
USPC .................................. 604/289, 290
See application file for complete search history.

(56) References Cited

U.S. PATENT DOCUMENTS

| | | | | |
|---|---|---|---|---|
| 5,071,104 A | * | 12/1991 | Witt et al. | 251/342 |
| 5,312,385 A | * | 5/1994 | Greco | 604/356 |
| 5,505,210 A | * | 4/1996 | Clement | 600/566 |
| 5,785,690 A | * | 7/1998 | Newman et al. | 604/180 |
| 2005/0016620 A1 | * | 1/2005 | Proulx et al. | 141/27 |

* cited by examiner

*Primary Examiner* — Melanie Hand
(74) *Attorney, Agent, or Firm* — Don Halgren

(57) ABSTRACT

A wound treatment arrangement for the debriding and cleansing of a patient's body portion comprising: a flexible elongated body portion enclosure bag; an elongated nozzle arrangement securable to the inner surface of the elongated enclosure bag; a pressurized fluid treatment supply gun; and a connectable and releasable coupler member arranged on the proximal end of the nozzle arrangement so as to sealably receive a corresponding coupler arrangement on the fluid treatment supply gun.

22 Claims, 4 Drawing Sheets

WOUND TREATMENT AND CONTAINMENT ARRANGEMENT

This application is a continuation-in-part application of patent application Ser. No. 11/232,456 filed 19 Oct. 2005, now U.S. Pat. No. 7,771,402, issued 10 Aug. 2010, which is a continuation-in-part application Ser. No. 10/684,960, filed 14 Oct. 2003, now abandoned which is a continuation-in-part application of patent application Ser. No. 09/621,636 filed Jul. 21, 2000 now U.S. Pat. No. 6,635,035, which is a continuation-in-part application of Ser. No. 09/561,978, filed May 2, 2000 now U.S. Pat. No. 6,562,013 which is a continuation-in-part application of Ser. No. 09/156,115, filed Sep. 18, 1998 now U.S. Pat. No. 6,083,209, which is a continuation-in-part of application Ser. No. 08/682,888, filed Jul. 11, 1996 now U.S. Pat. No. 5,848,998 each of which are incorporated herein by reference.

BACKGROUND OF THE INVENTION

1. Field of the Invention

The present invention relates to a closed irrigation system for the treatment of chronic wounds.

2. Prior Art

Wound treatment with its safe containment is a concept who's time has come. The increase in contamination and possible medical personnel injury is serious due to the increased size of the population having contagious diseases. The treatment process must also include means for safe disposal of any patient tissue and any treatment material or treatment fluids.

Wound management is a significant portion of all medical practice today. Wounds typically occur from burns, contamination from a blunt trauma, chronic ulceration, tandem laceration, abscesses, cavities to be drained, cellulitis, skin infections or irritation, open bone fracture, compound fracture, and pressure sores, and their potential for MRSA (Methicillin-resistant Staphylococcus) infection is high. Such wounds and their treatment constitute a large percentage of the treatment provided to medical patients. The number of methods for wound cleansing and debridement and have included wound cleansers such as povidone-iodide, hydrogen peroxide, acetic acid, and chlorinated solutions which however have cytotoxic effect on cells. Other types of wound cleaning and debridement include piston type syringe irrigation, whirlpool treatments, wet to dry saline gauze dressings, surgical/medical debridement, enzymatic debridement, absorbent dextranno-more microbeads and pulsed lavage.

That relatively new procedure in wound management mentioned hereinabove, pulsed lavage, utilizes a pulsating water-jet, which is directed toward the wound site, which method is fairly effective in removing debris and bacteria from those wounds.

Pulsed lavage irrigation devices typically utilize a cone shaped shield, having an open base which is placed over the wound. The shield is utilized to minimize splashing so as to protect the healthcare worker and to prevent aerosolization of body fluid. Typically a pan would be held against a lower portion of the skin of a patient being treated. A suction tube may be hung into the pan so as to drain out fluid. The fluid is typically saline or saline within antibiotic added for wound debridement and sterilization.

A number of such physical devices are shown in the prior art to isolate and permit treatment of certain wound sites. One such device is shown in U.S. Pat. No. 5,477,504 to Baker et al. showing a misting apparatus which comprises a container secured to a limb of a patient at each end, by a rigid cuff. The cuff is held onto the limb by a securement strap and each cuff has an opening to permit an elongated misting tool to be fixedly arranged there to. This apparatus may be satisfactory for replying a mist to a limb, for the prevention of that limb from drying out, but it has rigid conduits which limits the manipulation of the device, and which prevents it from being applied to a wide range of a debriding and cleansing actions. U.S. Pat. No. 5,312,385, issued to Greco shows a device for protected pulse irrigation. Greco requires a support structure for holding the enclosure away from the patient's body, yet provides no support for a nozzle or discharge gun arranged for interaction with the enclosure, thus requiring greater attention over the relationship between the nozzle and discharge gun during an operative procedure than should otherwise be required.

It is an object of the present invention to therefore overcome the disadvantages of the prior art.

It is a further object of the present invention to provide a closed irrigation system for the treatment of chronic wounds which permits attending medical personnel to carefully choose the location most appropriate for a nozzle to be inserted therethrough.

It is yet a further object of the present invention to provide a closed irrigation system for the treatment of chronic wounds which permits simple and safe adjustment of enclosure about a body portion of a patient.

It is still a further object of the present invention to provide a securement system for an irrigation gun so as to minimize the possibility of that irrigation gun from becoming loose or separated from the enclosure bag during a procedure.

It is yet a further object of the present invention to provide access by medical personnel to the inside of the enclosure bag during an operative procedure.

It is yet still a further object of the present invention to provide such access for medical personnel to the inside of the enclosure bag at any location on that bag as may be selected by the attending medical personnel.

It is yet another object of the present invention to provide an enclosure bag which permits clearer viewing and magnification and photographing of at least portions of the patient contained within that bag, by virtue of the material from which the enclosure bag is constructed.

It is a further object of the present invention to provide a wound or patient irrigation containment arrangement which maximizes the treatment capabilities of the medical personnel, and maximizes the safety considerations for those medical personnel.

It is yet a still further object of the present invention to provide a wound treatment system for providing a containment arrangement which is less irritating to the patient, which treatment system may be stabilized and maintained about the patient for an extended period of time.

It is yet a further object of the present invention to provide a wound containment system which is portable, to permit such use to be performed in the field, in a home or any environment where such a need occurs.

It is yet an important object of the present invention to provide a wound treatment arrangement, which may be utilized in a home or field setting which may utilize fluid pressure from a home faucet or shower head, and which treatment will not enlarge a wound being properly treated.

It is a still further object of the present invention provide a wound treatment arrangement wherein a nozzle from a fluid spray gun is prevented from being utilized beyond its first use.

It is still a further object of the present invention to provide a wound treatment arrangement wherein the location of a nozzle may be determined by the medical personnel immediately prior to such treatment taking place.

It is still yet a further object of the present invention to provide a wound treatment arrangement wherein a pressure fluid supply gun may be adapted to utilize a variety of manufacturers' nozzles.

BRIEF SUMMARY OF THE INVENTION

The present invention comprises an arrangement for enclosing a body portion of a patient by a flexible disposable transparent member such as an elongated bag having an opening at one or both ends or in a further embodiment, a flat or body-conformable shaped sheet of such material so as to properly enclose a treatment site on the patient to which that transparent member is secured.

In a first embodiment of the present invention, the transparent member comprises an elongated flexible, transparent bag having an opening at one end thereof for receipt of a patient's body part. The opened end of the elongated bag in this embodiment, may have a colored annular tape disposed therearound, and in engagement with the periphery of that opened end. The colored tape is adjustable so as to be secured to the opened end of the enclosure bag about the patient's body portion.

A lower portion of that elongated bag has a discharge port attached thereto. The discharge port includes a flexible conduit which is in fluid communication with a tissue treatment fluid collection bag. The transparent member, which in this embodiment is the elongated bag, has a hand access sleeve arranged at one or more locations within that transparent member. The hand access sleeve comprises an annular rim which surrounds one or more slits though the enclosure bag, the one or more slits being an overlapping relation so as to protect the containment integrity of the interior of the elongated bag.

The transparent member, that is, the enclosure bag, may have one or more treatment-gun-piercable receiving ports thereon. Those receiving ports may be installed by the attending personnel at any location on the bag, where necessary for the most effective use of the treatment gun through that enclosure bag. The receiving ports are comprised of an annular housing or sleeve secured at one end to a generally rigid flange member. A piercable membrane preferably extends across the rigid flange and the inner end of the annular housing or sleeve. The flange member in this embodiment may have a bag piercing nozzle extending therefrom which is utilized to pierce the enclosure bag so that the rigid flange may be attached thereto. The rigid flange has a lower side with adhesive thereon to facilitate securement of the flange to the selected site on the enclosure bag.

The annular housing or sleeve may have an inner surface with a "bayonet-type" gun lock, to permit rotative interlocking mating between the treatment gun and the annular housing to avoid miss-spraying of treatment fluid or loss of compression within that enclosure bag when/if that enclosure bag is pressurized. The treatment gun provides a pressurized treatment fluid such as saline or the like with any appropriate medicaments of therewith, to act so as to debride a wound on the patient. The treatment gun may also be an air pressure source which is controllable as to flow rate, temperature and constituent mix, so as to pressurize the enclosure bag as necessary to maintain a proper spacing of the bag from the patient's wound site, and to increase the discharge rate of patient contaminated fluid through the discharge tube into the collection bag. The material for the bag itself is preferably comprised of an anti-fog material such as for example, a silicone polymer, which is hydrophilic.

The present invention may also comprise a flexible enclosure bag which includes a sealed single or multi lumen tube which is articulably disposed through a portion of the bag. The tube has a distalmost end having a spray nozzle thereat. That spray nozzle may be removable and changeable through the "patient-receiving" open end of the disposable bag, as conditions may require.

The multi lumen or single lumen treatment fluid supply tube extending through the disposable bag, may have a proximal end with an adapter which is attachable to a distal end of an irrigator gun. The irrigator gun may have a pump therein, to facilitate regulation/control of a fluid or a treatment additive supply being pumped therethrough. The irrigator gun for safety reasons, would preferably have a battery driven motor so as to not electrically endanger any attending personnel.

The manipulable irrigator or treatment gun is supplied by treatment fluid through a conduit from a fluid source. That fluid source may comprise for example, a portable reservoir, a shower head as found in a home setting, or that fluid source may comprise a bathtub faucet or a sink faucet. That conduit to the irrigator gun would have a proximal or supply end with a flexible fluid source adaptor thereon to permit attachable mating of that fluid source to that treatment fluid supply conduit.

The disposable enclosure bag and tip arrangement portion of the present embodiment of the invention will preferably have a suction-free gravity fed drainage tube extending from a lower end thereof, to a collection bag. Suction may damage the wound during any treatment causing pain to the patient. A variably pressurizable enclosure bag could be utilized to facilitate the drainage however, into the collection bag, the pressurized atmosphere having a controlled air source located in the tip of the treatment gun.

The drain channel will also have a one way valve, such as a "duck bill" valve arranged therein to prevent any backflow or backwash of the fluid and debris which was washed from the patient's wound.

The tube extending through the disposable bag, with the nozzle on its distalmost end, is articulable by virtue of the flexibility of the disposable bag and the seal between the tube and its received port through which it extends.

The fluid conduit to the irrigation gun may also be connected to a fluid source such as a tank or reservoir which might be transportable in an automobile, an ambulance or other vehicle transported to a field site for use in emergency situations. Immediate contained spray-cleaning of wounds from potential contaminants, poisons or other hazard materials, in a non-wound enlarging manner, and collection of that debris for testing and or safe disposal provides optimum care to a patient not found or considered by the prior art.

The present invention in a further set of embodiments may also comprise elongated body component enclosable, disposable flexible bag having a body insertable opening on at least one end thereof. At least one built-in treatment fluid nozzle distribution arrangement may be disposed within and through the surface of the flexible bag, having an elongated nozzle extending inwardly from the inside of the bag. The proximal end of the built-in nozzle is preferably fixedly attached to the surface of the bag, having a removable seal thereover, for cleanliness purposes. The seal, once removed, permits the insertion, in a bayonet type of arrangement for receipt of the distal end of a pressurized fluid wound treatment gun. The pressurized wound treatment gun preferably has an adjustable trigger mechanism to permit an adjustable flow rate of wound treatment of fluid and/or medicaments therethrough.

The flexible bag in this embodiment also preferably has an elongated discharge tube in at least one location on a lower edge thereof. The discharge tube may feed through a one-way valve, such as for example, a duck bill valve, into a solid tissue waste treatment collection bag. The waste treatment collection bag preferably includes a solidifier within that collection bag. That solidifier may be held in a closed reservoir within the collection bag, awaiting an internal tear seal or dissolution, to be opened or dissolved upon use of the flexible collection bag.

A piercable sample port may be arranged at one or more locations on the waste collection bag to permit needle sampling of the tissue which has been collected therewithin. The collection bag with its solidified body tissue therewithin may be thrown in a waste collection unit by merely cutting the discharge tube on the side opposite the one way duckbill valve.

A yet further embodiment of the present invention comprises a removable nozzle arrangement on the pressure treatment gun, wherein a removable nozzle has a pair of articulated barbs, to prevent the nozzle from being pulled out and thus removed from a patient limb-enclosable flexible bag, once that nozzle has been inserted therein. Those barbs would act as a stop, and thus prevent the nozzle from being removed from a patient treatment bag once it had already been inserted and used therein.

The invention thus also comprises a wound treatment arrangement for the debriding and cleansing of a patient's body portion comprising: a flexible elongated body portion enclosure bag; an elongated nozzle arrangement securable to the inner surface of the elongated enclosure bag; a pressurized fluid treatment supply gun; and a connectable and releasable coupler member arranged on the proximal end of the nozzle arrangement so as to sealably receive a corresponding coupler arrangement on the fluid treatment supply gun. The enclosure bag may also include a tissue collection bag. The tissue collection bag preferably has a one-way valve arranged between the enclosure bag leading thereto. The tissue collection bag preferably may include a multilayered, piercable sample port. The fluid treatment supply gun may have a removable nozzle thereon. The removable nozzle may have an articulated barb thereon to prevent the nozzle from being removed from the containment bag after it has been utilized for treatment of a patient's body portion. The fluid treatment supply gun may have a coupler adapter thereon for receipt of any of a variety of manufacturers' nozzles thereon. The fluid treatment supply gun may have a coupler adapter with a medicament supply conduit and reservoir attached thereto for independent supply of medicament to any wound being treated through the nozzle attached to the adapter. The collection bag may include a contained and releasable solidifier therein, which is releasable within the collection bag by dissolution of a surface coating on the solidifier, or by external pressure frangeably applied to that collection bag. The fluid treatment supply gun may have a coupler adapter thereon to permit adaptive receipt of a variety of manufacturers' nozzles thereon. The fluid treatment supply gun may have a coupler adapter with a medicament supply conduit and reservoir attached thereto for independent supply of medicament to any wound treatment fluid being passed through the nozzle attached to the adapter. The collection bag may include a contained and releasable solidifier therein, which is releasable within the collection bag by external pressure applied to that collection bag. The collection bag may include a biocide and solidifier having a dissolvable coating thereon, for dissolution of the coating upon collection of tissue and fluids within the collection bag. The collection bag may have a magnification member on the surface of the bag to provide light focusing and to enhance viewing of the patient's body portion therein. The magnification member may comprise an appliqué attached to the bag, on the outer or inner surface thereof, or the magnification member may be formed into the bag during the bag's manufacture by a heat and pressure process.

BRIEF DESCRIPTION OF THE DRAWINGS

The objects and advantages of the present invention will become more apparent when viewed in conjunction with the following drawings, in which.

DETAILED DESCRIPTION OF THE INVENTION

Figure 1:
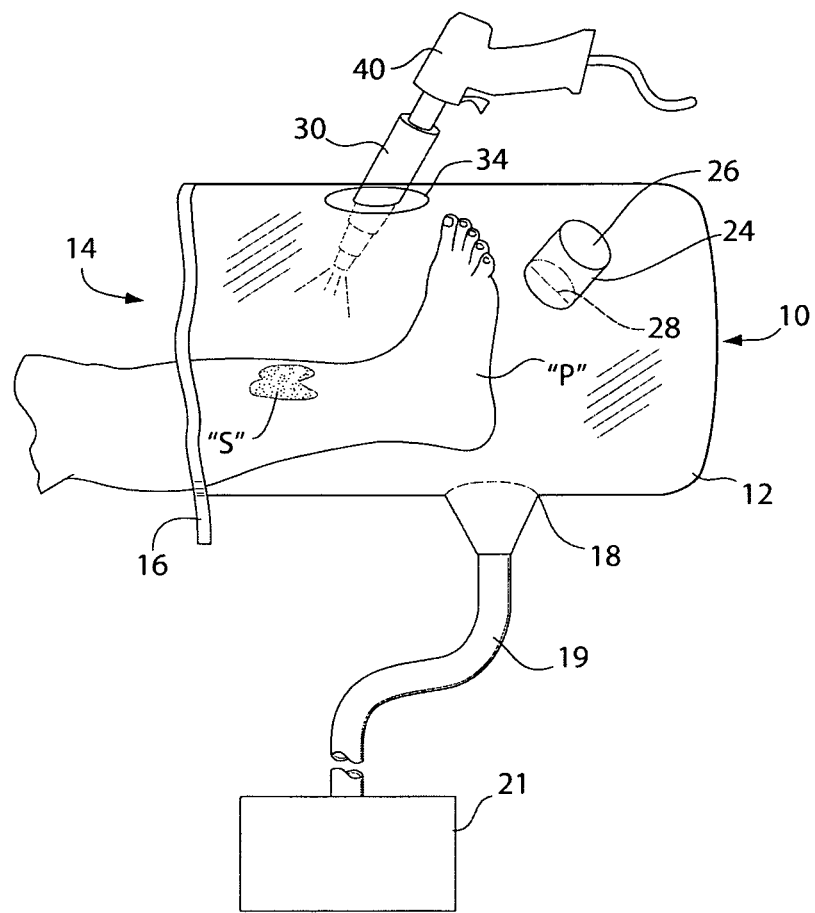
FIG. 1 is a schematic representation of a patient body part in an enclosure bag with a treatment gun housing shown thereattached, together with a hand access sleeve through that bag.

Referring now to the drawings in detail, and particularly to FIG. 1, there is shown the present invention which comprises a containment arrangement for closing about a body portion of a patient "P" by a flexible, disposable transparent member 10 such as an elongated bag 12 having an opening at one or both ends or a flat or body-conformable-shaped sheet of such material so as to properly enclose/contain a treatment site "S" on the patient "P" to which that transparent member or bag 10/12 is secured.

In a first embodiment of the present invention, the transparent member 10 comprises the elongated bag 12 having an opening 14 at one end thereof for receipt of a patient's body part. The opened end 14 of the elongated bag 12 in this embodiment, may have a colored annular ribbon or tape 16 disposed therearound, and in engagement with the periphery of that opened end 14. The colored tape 16 is adjustable so as to be tied into a knot or adhered by adhesive, so as to closely secure the opened end of the enclosure bag 12 about the patient's body portion.

A lower portion of that elongated bag has a preferably funnel-shaped treatment fluid discharge port 18 attached thereto. The discharge port 18 has a flexible conduit 20 which is in fluid communication with a lower collection bag 22, as represented in FIG. 1. The transparent containment member 10, which in this embodiment is the elongated bag 12, may have a hand-access-sleeve 24 arranged at one or more locations within that transparent member 10. The hand access sleeve 24 comprises an annular rim 26 which surrounds one or more slits 28 though the enclosure bag 12, the one or more slits 28 preferably being in for example, an overlapping or non-parallel and multilayered relation so as to protect the containment integrity of the interior of the elongated bag 12, while permitting the insertion of a medical personnel worker's arm therethrough.

Figure 2:
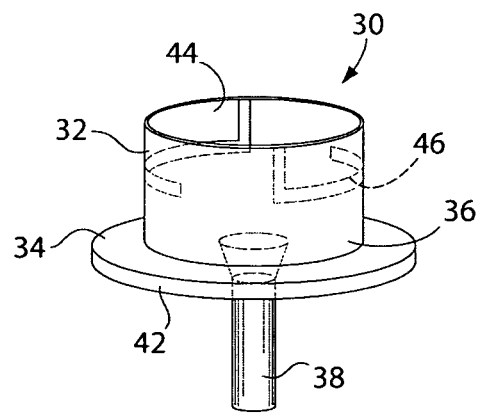
FIG. 2 is a perspective view of the treatment gun receiving housing shown in FIG. 1 with a bag piercing fluid dispersing nozzle extending therefrom.

The transparent member, that is, the enclosure bag 12 preferably has one or more treatment-gun-receiving ports 30 thereon. Those receiving ports 30 may be installed by the attending personnel at any location on the bag 12, where necessary for the most effective use of a treatment gun 40 through that enclosure bag 12. The enclosure ports 30 are comprised of an annular housing or sleeve 32 secured at one end to a generally rigid flange member 34, as represented in FIG. 1. A piercable membrane 36 may also extend across the rigid flange 34 and the inner end of the annular housing or sleeve 32, as represented in FIG. 2. The piercable membrane 36 may preferably include a bag piercing nozzle 38 extending therefrom which is utilized to pierce the enclosure bag 12 so that the rigid flange 34 may be attached thereto, as represented in FIG. 2. The rigid flange 34 has a lower side 42 with adhesive thereon to facilitate a securement to that site on the enclosure bag 12.

The annular housing or sleeve 32 in this embodiment preferably has an inner surface 44 with a female "bayonet-type" gun lock 46, to permit interlocking mating between a treatment gun 40 having a corresponding male, "bayonete-type" distal member thereon, to permit simple rotative engagement between the gun 40 and its port 30, on or through the annular housing 32, and to avoid miss-spraying of treatment fluid or loss of compression within that enclosure bag 12 if that enclosure bag 12 is pressurized. The treatment gun 40 may be also arranged to provide a pressurized treatment fluid such as saline or the like with any appropriate medicaments of therewith, to act so as to debride a wound "S" on the patient "P", as represented in FIG. 1. The treatment gun 40 may also have an air pressure source therewith, which air source is controllable as to flow rate, temperature and constituent mix, so as to pressurize the enclosure bag 12 as necessary to maintain a proper spacing of the bag from the patient's wound site, to permit medical personnel access to the wound "S", and/or to increase the discharge rate of patient contaminated fluid through the discharge tube 19 into the collection bag 21, as represented in FIG. 1. The material for the bag 12 itself is preferably comprised of an anti-fog plastic such as a silicone, which is hydrophilic.

Figure 3:
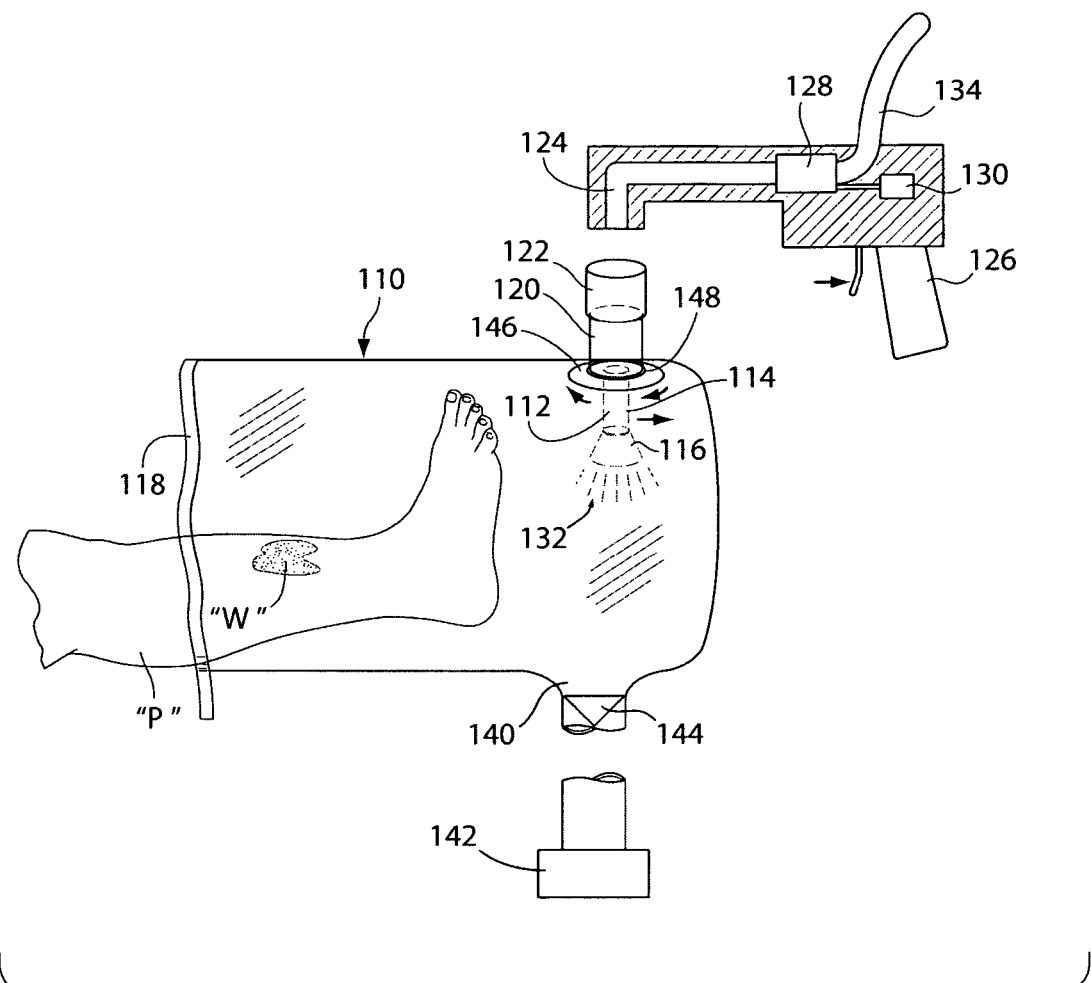
FIG. 3 is a schematic representation of a patient-securable, disposable, containment bag with an articulable nozzle therewithin, and a representation of an adjustable, treatment fluid dispensing gun.
Figure 4:
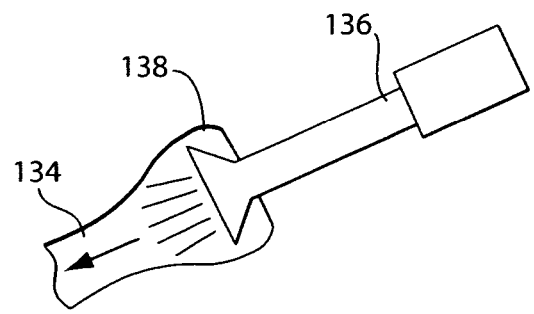
FIG. 4 is a schematic representation of a treatment fluid receiving conduit attached to a fluid source with a fluid source adapter thereon, which conduit would be a feed supply to the adjustable, treatment fluid dispensing gun.

Referring again to the drawings in detail, and particularly to FIGS. 3 and 4, there is shown a further preferred embodiment of the present invention which comprises a flexible bag enclosure 110 which is disposable, and attachable around or next to the wound site "W" of a patient "P". The disposable bag 110 includes a sealed single or multi lumen tube 112 which is articulably disposed through a portion of the bag 110. The multi-lumen of tube 112 may provide one or more medicaments to the treatment site, through the bag 110. The tube 112 has a distalmost end 114 having a spray nozzle 116 thereat, as represented in FIG. 3. That spray nozzle 116 may be removable and changeable through the open end 118 of the disposable bag 110, as conditions may require.

The multi lumen or single lumen tube 112 extending through the disposable bag 110 has a proximal end 120 with a adjustable adapter 122 which is attachable to a distal end 124 of an irrigator or treatment gun 126, as represented in FIG. 3. The irrigator or treatment gun 126 may have a controlled pump and/or controlled heater 128 therein, to facilitate regulation/control of a fluid or additive supply being pumped therethrough. The irrigator gun 126 for safety reasons, would preferably have a battery driven motor 130 so as to not endanger any attending personnel.

The manipulable irrigator or treatment gun 126 is supplied by treatment fluid 132 through a conduit 134 from a fluid source 136. That fluid source 136 may comprise for example, a shower head as found in a home setting, as represented in FIG. 4, or that fluid source may also be comprised of a bathtub faucet or a sink faucet. That conduit 134 to the irrigator gun 126 would have a distal end with a flexible fluid source adaptor 138 thereon to permit attachable enclosure of the distal end of the fluid source 136 (i.e. shower head) to that conduit 134, as represented in FIGS. 3, 4, 7 and 8.

The disposable bag 110 and nozzle tube arrangement 112 may have a suction-free gravity fed drainage tube 140 extending from a lower end thereof, to a collection bag 142, as represented in FIG. 3. Gravity is used because suction might damage the wound "W" during any treatment. The containment bag 110 may however be pressurized with oxygen or other medicated gases to hold the containment bag 110 a spaced distance from the surface of the patient "P" and to help push and thus flush the wound debris into the collection bag 144 faster.

Figure 6:
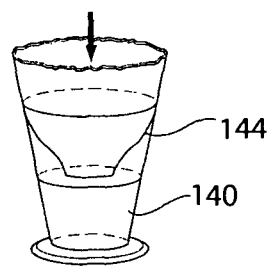
FIG. 6 is a further embodiment of the disposable bag drain channel and one way valve therewithin, showing a distalmost generally rigid drain-engaging discharge end, for forced receipt and discharge of used wound treatment fluids and debris into a sink or tub drain or collection bag opening.

The drain channel 140 shown in FIGS. 3 and 6, will also have a one way valve 144, such as a "duck bill" valve arranged therein to prevent any backflow or backwash of the fluid and debris which was washed from the patient's wound "W".

The tube 112 extending through the disposable enclosure bag, with the nozzle 116 on its distalmost end, is articulable by virtue of the flexibility of the disposable bag 110 and the flexible or articulable seal 146 between the tube 112 and its receiving port 148 through which it extends, as shown in FIG. 3.

Figure 5:
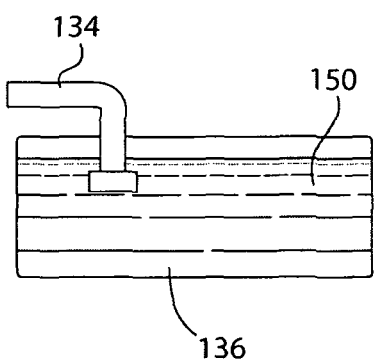
FIG. 5 is a schematic representation of the proximal end of the treatment fluid supply conduit taking fluid from a reservoir or tank, which would be thus supplied to the adjustable fluid dispensing gun.

As represented in FIG. 5, the fluid conduit 134 to the irrigation gun 126 may also be connected to a fluid source 136 such as for example, a tank or reservoir 150 which might be found in an automobile, an ambulance or other vehicle transported to a field site for use in emergency situations. Thus, immediate cleaning of wounds from potential contaminants, poisons or other hazard materials, in a non wound-enlarging manner, and collection of that debris for testing and or safe disposal thereof, at the site of an accident thus provides optimum care to a patient not found or considered by the prior art.

Figure 7:
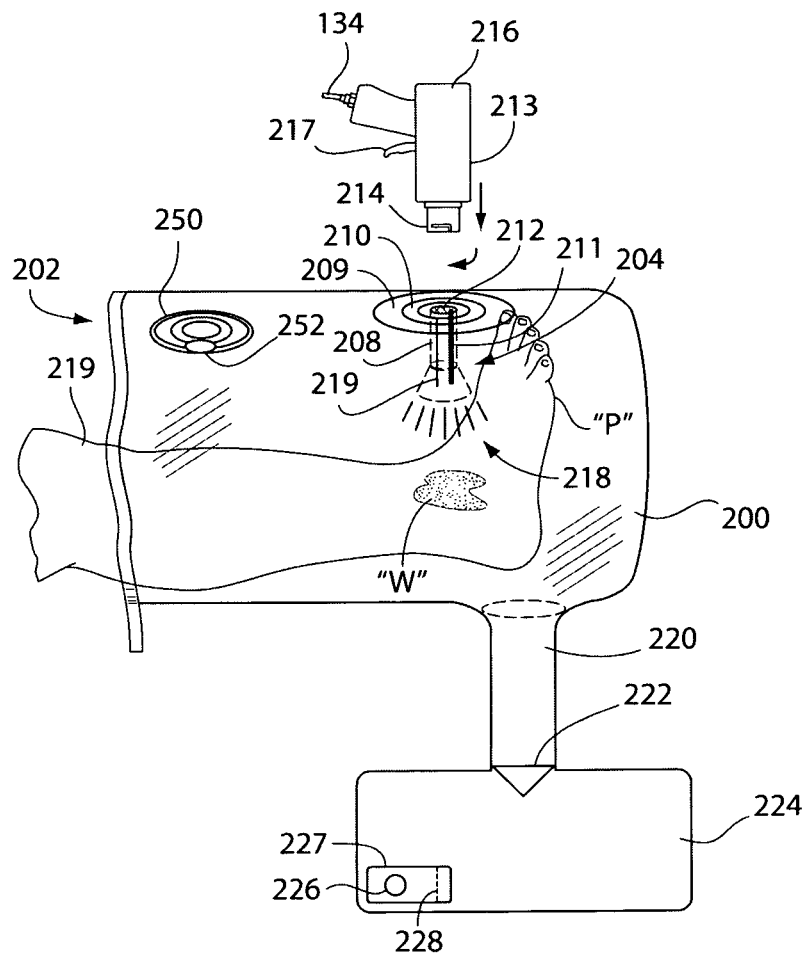
FIG. 7 is a further embodiment of a disposable bag arrangement with a fixed internal nozzle, matable with a the bayonet grip of spray treatment gun.

The present invention in a further set of embodiments may also comprise elongated body component enclosable, disposable flexible bag 200 as represented in FIG. 7. The body component enclosable, disposable flexible bag 200 has a body insertable opening 202 on at least one end thereof, as represented in FIG. 7. At least one nozzle arrangement 204 may be disposed within and through the surface 206 of the flexible bag 200, having an elongated nozzle 208 extending inwardly from the bag 200.

In one preferred embodiment of the nozzle arrangement 204 of the present invention, such nozzle arrangement 204 may be moved to a desired site within the bag 200 by the medical personnel and attached thereto by an aggressive adhesive on a flange 209 on the proximal end 210 of the nozzle arrangement 204. In another embodiment of the present invention, the proximal end 210 of the nozzle arrangement 204 could be built-in to a desired central location of the bag 200, which nozzle arrangement 204 is preferably fixedly attached through the surface 206 of the bag, the proximal end 210 of the nozzle arrangement 204 having a removable seal 212 thereover, for cleanliness purposes. The seal 212, once removed, permits the secured leak proof insertion, in a female threaded manner or a bayonet type of arrangement, of a corresponding male threaded coupler end (or a bayonet end) 214 on the distal end of a pressurized fluid wound treatment gun 216. The pressurized wound treatment gun 216 may have an adjustable trigger mechanism 217 to permit an adjustable volume flow rate of sprayed wound treatment of fluid 218 therethrough.

The flexible bag 200, as represented in FIG. 7 in this embodiment also preferably has an elongated discharge tube 220 in at least one location on a lower edge thereof. The discharge tube 220 may feed through a one-way valve 222, such as for example, a duck bill valve, into a solid tissue waste treatment collection bag 224. The waste treatment collection bag 224 preferably includes a solidifier 226 within that collection bag 224. That solidifier 226 may be held in a closed frangible reservoir 227 within the collection bag 224, awaiting an internal tear seal 228, as part of the side of the bag 224, enclosing the solidifier 226, to be opened only upon use of the flexible bag 200, or the solidifier may be encased in a dissolvable casing awaiting receipt of fluids into the collection bag 224. Such a solidifier may comprise for example, 120 gr of sodiumdichloro-5 trazinetrione (10%) and chlorine (5.8%), or Microtech's Isolyset 3000™.

A multilayered, piercable sample port 230 may be arranged at one or more locations on the waste collection bag 224, to permit needle sampling of the waste tissue "T" which has been collected therewithin. The collection bag 224 with its solidified body tissue "T" therewithin may be thrown in a waste collection unit by merely cutting the discharge tube 220 on the side opposite the one way duckbill valve 222, closest to the now used-up flexible bag 200.

Figure 8:
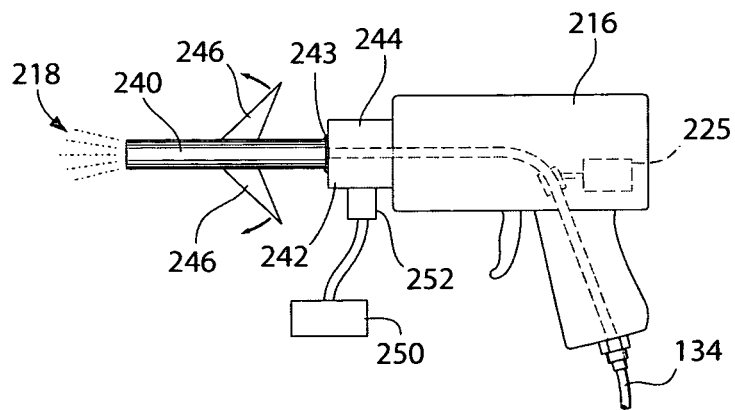
FIG. 8 is a side elevational view of spray treatment gun with a nozzle securing arrangement for preventing re-use thereof.

A yet further embodiment of the present invention is shown in FIG. 8, wherein a removable nozzle arrangement 240 is shown removably connected by a twist or screw coupler 242 to the discharge end 244 of the pressure treatment gun 216. The coupler 242 may comprises a flexible elastomeric flanged adaptor 243 to permit the snug attachment of any of several different manufacturer's nozzles onto this gun 216. The coupler 242 itself may also preferably have a removable controlled flow valve connection 252 to a medicament supply 250 to permit certain medicaments to be fed through the nozzle 240 during the fluid treatment of the patient's body portion within the containment bag 200. This eliminates the need for pharmacists to separately add medicaments to the saline treatment fluid being utilized by the treatment gun 216.

The aforementioned removable nozzle arrangement 240, as represented in FIG. 8, preferably has a pair of spring loaded articulated barbs 246 biasable outwardly once the nozzle arrangement 240 has been inserted into a patient member containment bag 200, to prevent the nozzle arrangement 240 from being removed from the patient limb-enclosable flexible bag 200, once it has been inserted and used therein. Those self actuating barbs 246, snap outwardly after triggered insertion into the bag 200, and would act as a removal stop, and thus prevent the nozzle arrangement 240 from being removed from a patient treatment bag 200 once it had already been inserted therein. Such nozzle 240 would be untwisted or "un-bayoneted" from the coupler 242.

Shown in FIG. 7 is a plastic "magnification" appliqué 250 for enhancing or magnifying the wound's visualization on the patient's limb, and for permitting clearer analysis and photographic recordation thereof. Such appliqué may be adhered to the inside or outside of the surface of the treatment bag 200, or molded therein as part of the manufacturing process thereof. The appliqué 250 may have an adapter 252 thereon for securement of LED lights and/or an electronic camera, not shown for clarity of the figures.

The nozzle 208, represented in FIG. 7, in a further embodiment thereof, may include an "energy" or light transmitting fiber or conduit 211 extending longitudinally therealong, from a proximal location at its juncture at the bag 200 to the distal tip thereof. The energy may for example, be comprised of magnetic energy, light energy, heat energy, electrical energy or ultrasound energy. The energy would preferably be transmitted through the conduit 211 may be received from an energy source, as for example, a light source 213 adjacent the coupler 214 on the gun 216. The light transmitted may be for illuminating the wound being treated within the bag 200, or for light treatment of the wound itself, so as to accomplish a biological assay to indicate bacteria levels on the wound, such light comprising for example: ultra violet (UV) light, or infra red (IR) light, from the source 213 within the gun 216, or transmitted therethrough. Further, fluorescein for example, may be transmitted from a separate lumen 219 within the elongated nozzle 208, or pre-loaded within the nozzle 208 prior to its initial use, to help indicate those bacteria levels of concern on the wound "W".

The sprayed treatment fluid 218 may in a yet further embodiment, may be controllably pulsed by a pressure control computer arrangement 225 within the gun 216, as represented in FIG. 8. The computer arrangement 225 could be programmed to control flow of treatment fluid through the gun 200, so as to generate particular waves, or even cycles of pressure of that treatment fluid 218, as may be required for hydro-mechanically treating different types of wounds, such as soft tissue, bone or the like.

The invention claimed is:

1. A wound treatment arrangement for the enclosed, safe debridement of a patient's wound, comprising:
    an elongated enclosure bag for enclosing at least part of a patient being treated, the bag having at least one open end;
    a selectively placable treatment gun-receiving-housing having an annular housing for mating with a pressurized treatment gun, the housing having a pressure maintaining gun-locking arrangement therewith, which pressure maintaining arrangement comprises a nozzle with a proximal end having a coupler member thereon for enabling the connecting and releasing of a corresponding coupler arrangement on the pressure treatment gun; and
    a lower debris drain arranged in the lower side of the enclosure bag.

2. The wound treatment arrangement as recited in claim 1, including a hand access port arranged through the enclosure port, separate from the open end of the bag, wherein the hand access port comprises an annular sleeve with an annular flange at one end thereof, the flange having an adhesive on a lower side thereof for adhesion to the bag.

3. The wound treatment arrangement as recited in claim 2, wherein the annular flange has a membrane thereacross, the membrane also having a slit thereacross, for attachment of the flange to the bag in encircling non-alignment with an existing slit in the bag, to sealably permit hand access through non-parallel slits into the bag for medical access to a treatment site.

4. The wound treatment arrangement as recited in claim 1, wherein the gun receiving housing has a treatment fluid applying nozzle for fluid communication with a gun secured to the gun-locking arrangement in the gun-receiving housing.

5. The wound treatment arrangement as recited in claim 1, including a colored tape arranged at the open end of the enclosure bag for securable adjustment of the open end of the bag to the patient.

6. A non wound-enlarging treatment system for cleansing of a wound site on a patient, comprising:
- a disposable wound enclosing bag;
- a gravity-fed drain conduit extending from the bag;
- a nozzle wand fixedly attached through a side of the bag; and an attachable fluid supply gun having a coupler member thereon for connectable and releasable engagement to a corresponding coupler member on a proximal end of the nozzle wand fixedly attached to the side of the bag, the connectable and releasable fluid supply gun thus enabling a connectable and releasable supply of wound treatment fluid to the wound site within the bag.

7. The treatment arrangement as recited in claim 6, wherein the wound treatment fluid comes from a faucet.

8. The wound treatment arrangement as recited in claim 6, wherein the bag and nozzle wand are disposable.

9. The wound treatment arrangement as recited in claim 6, wherein the wound treatment fluid from the fluid supply gun includes pressurized air to assist gravity in removing debris from the wound enclosing bag.

10. The wound treatment arrangement as recited in claim 6, wherein the enclosure bag has a hand access port attached thereto for enabling hand access through the bag for further wound treatment during a debridement action.

11. A wound treatment arrangement for the debriding and cleansing of a patient's body portion comprising:
- a flexible elongated body portion enclosure bag;
- an elongated nozzle arrangement securable to the inner surface of the elongated enclosure bag;
- a pressurized fluid treatment supply gun; and
- a connectable and releasable coupler member arranged on the proximal end of the nozzle arrangement so as to sealably receive a corresponding coupler arrangement on the fluid treatment supply gun.

12. The wound treatment arrangement as recited in claim 11, wherein the enclosure bag also includes a tissue collection bag.

13. The wound treatment arrangement as recited in claim 12, wherein the tissue collection bag has a one-way valve arranged between the enclosure bag leading thereto.

14. The wound treatment arrangement as recited in claim 11, wherein the tissue collection bag includes a multilayered piercable sample port.

15. The wound treatment arrangement as recited in claim 11, wherein the fluid treatment supply gun has a removable nozzle thereon.

16. The wound treatment arrangement as recited in claim 15, wherein the removable nozzle has an articulated barb thereon to prevent the nozzle from being removed from the containment bag after it has been utilized on a patient's body portion.

17. The wound treatment arrangement as recited in claim 15, wherein the fluid treatment supply gun has a coupler adapter thereon to permit adaptive receipt of a variety of manufacturers' nozzles thereon.

18. The wound treatment arrangement as recited in claim 15, wherein the fluid treatment supply gun has a coupler adapter with a medicament supply conduit and reservoir attached thereto for independent supply of medicament to any wound treatment fluid being passed through the nozzle attached to the adapter.

19. The wound treatment arrangement as recited in claim 15, wherein the collection bag includes a contained and releasable solidifier therein, which is releasable within the collection bag by external pressure applied to that collection bag.

20. The wound treatment arrangement as recited in claim 15, wherein the collection bag includes a biocide and solidifier having a dissolvable coating thereon, for dissolution of the coating upon collection of tissue and fluids within the collection bag.

21. The wound treatment arrangement as recited in claim 11, wherein the collection bag has a magnification member on the surface of the bag to enhance viewing of the patient's body portion therein.

22. The wound treatment arrangement as recited in claim 21, wherein the magnification member comprises an appliqué attached to the bag.

* * * * *